United States Patent [19]
Venktrama et al.

[11] Patent Number: 5,273,755
[45] Date of Patent: Dec. 28, 1993

[54] TRANSDERMAL DRUG DELIVERY DEVICE USING A POLYMER-FILLED MICROPOROUS MEMBRANE TO ACHIEVE DELAYED ONSET

[75] Inventors: Subbu S. Venktrama, Palo Alto; Renee A. Fallon, Sunnyvale; Gary W. Cleary, San Mateo, all of Calif.

[73] Assignee: Cygnus Therapeutic Systems, Redwood City, Calif.

[21] Appl. No.: 748,934

[22] Filed: Aug. 23, 1991

[51] Int. Cl.⁵ .................................... A61F 13/02
[52] U.S. Cl. ................................ 424/448; 424/447; 424/449
[58] Field of Search .............. 424/449, 448, 447

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,742,951 | 7/1973 | Zaffaroni | 128/260 |
| 3,797,494 | 3/1974 | Zaffaroni | 424/448 |
| 4,286,592 | 9/1981 | Chandrasekaran | 128/260 |
| 4,533,540 | 8/1985 | Blank | 424/28 |
| 4,559,222 | 12/1985 | Enscore et al. | 424/28 |
| 4,618,699 | 10/1986 | Fialla | 560/86 |
| 4,650,484 | 3/1987 | Shaw | 424/448 |
| 4,655,766 | 4/1987 | Theeuwes et al. | 604/896 |
| 4,661,441 | 4/1987 | Kajiwara et al. | 430/555 |
| 4,681,584 | 7/1987 | Gale | 424/449 |
| 4,751,087 | 6/1988 | Wick | 424/449 |
| 4,776,850 | 10/1988 | Guse et al. | 604/304 |
| 4,778,678 | 10/1988 | Guse et al. | 424/487 |
| 4,784,857 | 11/1988 | Berry et al. | 424/449 |
| 4,786,282 | 11/1988 | Wagle et al. | 604/307 |
| 4,801,458 | 1/1989 | Hidala | 424/449 |
| 4,849,224 | 7/1989 | Chang | 424/449 |
| 4,917,676 | 4/1990 | Heiber | 424/449 |
| 4,956,181 | 9/1990 | Bayer | 424/447 |
| 4,971,799 | 11/1990 | Nakagawa | 424/448 |

Primary Examiner—Thurman K. Page
Assistant Examiner—D. Gabrielle Phelan
Attorney, Agent, or Firm—Morrison & Foerster

[57] ABSTRACT

A delayed onset transdermal drug delivery device exhibiting a delay period of at least six hours comprising a laminated composite of (12) a top backing layer; (13) a pressure rupturable layer underlying (12); (14) a reservoir of a solution of drug in a liquid vehicle between (12) and (13); (16) a wick layer underlying (13) for dispersing the drug once (13( is ruptured; (17) a polymer layer underlying (16) that is permeable to the drug; (18) a microporous membrane underlying (17) which is itself impermeable to the drug but whose pores are filled with a polymer that is immiscible in the adhesive and has a solubility parameter within two units of the solubility parameter of the vehicle; and (20) an adhesive layer underlying (18) that is permeable to the drug but is immiscible in the polymer filling the pores of (6).

18 Claims, 2 Drawing Sheets

5,273,755

TRANSDERMAL DRUG DELIVERY DEVICE USING A POLYMER-FILLED MICROPOROUS MEMBRANE TO ACHIEVE DELAYED ONSET

TECHNICAL FIELD

This invention is in the general field of transdermal drug delivery and relates specifically to devices from which drug is released in a delayed pattern from the time the device is placed on the skin. Devices that release drug in such a pattern are commonly referred to as "delayed onset" devices.

BACKGROUND

Earnest efforts to develop transdermal drug delivery devices that provide drug to the patient in a controlled pattern began in the late 1960s and early 1970s. The principal pattern of delivery that was investigated was substantially constant rate delivery in which delivery began at or shortly after the device was applied to the skin, rose to a desired level, and stayed at that level for a sustained time period. These efforts resulted in numerous patents being issued for devices of various structures that achieved or closely mimicked constant rate delivery. See, for instance, U.S. Pat. Nos. 3,598,122; 3,598,123; 3,797,494; and 4,286,592.

Nitroglycerin (NTG) is among the many drugs that has been administered transdermally. Among the U.S. patents describing transdermal NTG delivery are U.S. Pat. Nos. 3,742,951; 4,533,540; 4,559,222; 4,618,699; 4,681,584; 4,654,209; 4,655,766; 4,661,441; 4,751,087; 4,776,850;, 4,778,678; 4,784,857; and 4,786,282. None of these patents concern delayed onset nitroglycerin delivery. Further, the initial commercial transdermal NTG devices (the Transderm-Nitro and Nitro-Dur devices) are continuous rather than delayed-onset delivery devices.

In the mid-1980s a number of clinical studies raised questions about the efficacy of NTG therapy provided by the then available commercial transdermal devices that administered NTG in a continuous pattern. Specifically, continuous administration was tending to cause tolerance and hemodynamic attenuation. This led clinicians to conclude that the ideal regimen for administering NTG would include an overnight "washout period" during which no NTG was administered. Correlatively, it led developers of transdermal devices to propose delayed onset devices for administering NTG.

U.S. Pat. No. 4,956,181 describes a delayed onset device for administering NTG. Its device consists of a backing layer, a rupturable pod sandwiched between the backing and a nonwoven fabric layer, a barrier membrane, an adhesive layer, and a release liner. The rupturable pod contains NTG and an activator liquid that is capable of plasticizing the barrier membrane and increasing its permeability to NTG. Once the pod is ruptured, drug and activator migrate down through the barrier membrane, with the activator causing the membrane to become increasingly permeable to the drug. While this patent indicates that an effective delay of up to 12 hr may be achieved, the examples of the patent describe devices that achieve only a 4-6 hr delay.

An object of the present invention is to provide a delayed onset device for administering NTG that provides at least a six and preferably an eight hour delay in administration. The device of the invention does not use plasticization of a barrier membrane as a delay mechanism.

DISCLOSURE OF THE INVENTION

This invention is a device for administering a drug transdermally following application of the device to a subject's skin wherein the delivery of drug is delayed at least about six hours after said application comprising in combination: (a) a nonrupturable backing layer forming the top surface of the device; (b) a pressure rupturable reservoir underlying (a) and containing the drug dissolved in a liquid vehicle; (c) a wick layer underlying (b) for dispersing the drug once the reservoir is ruptured; (d) a layer of a drug permeable polymer underlying (c); (e) a microporous membrane underlying (d); (f) a layer of a drug permeable adhesive polymer underlying (e) and forming the basal layer of the device wherein the pores of the membrane are filled with a polymer that is immiscible in the polymer of (d) and (f) and has a solubility parameter that is within two units of the solubility parameter of the vehicle; and wherein it initially takes at least about six hours for the drug to diffuse to the skin from the reservoir once the reservoir is ruptured and the device is applied to the skin.

MODES FOR CARRYING OUT THE INVENTION

Figure 1:
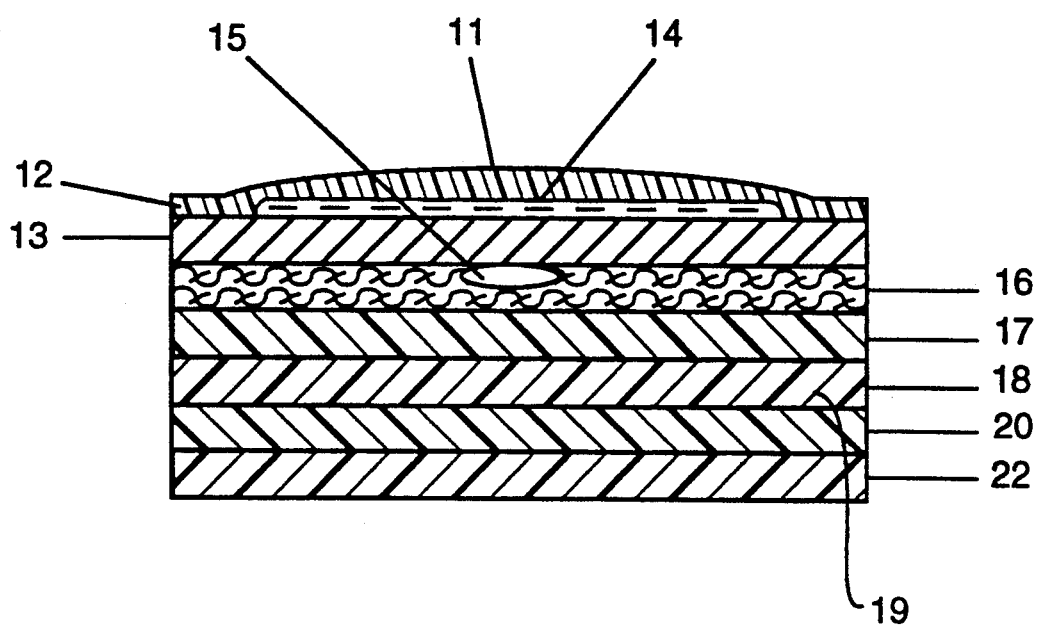
FIG. 1 is a sectional view of an embodiment of the invention for administering NTG. The drawing is not to scale. The thicknesses of the layers of the embodiment are exaggerated for the purposes of illustration.

The drawing shows a preferred embodiment, generally designated 11, of the delayed onset device of the invention. The top surface of the device is defined by backing layer 12. It is made of a material or combination of materials that is substantially impermeable to the solution of NTG in the liquid vehicle, does not absorb significant amounts of the NTG solution, and is capable of being sealingly bonded (e.g., by heat sealing or crimping) at its periphery to the underlying microporous membrane layer 18 (described below). In addition, the mechanical properties of the backing should be such that it does not rupture coincident with the rupture of the underlying rupturable layer 13. It is also preferably flexible and/or elastomeric. Examples of materials from which the backing layer may be formed are elastomeric polymers such as polyether block amide copolymers (e.g., PEBAX copolymers), polyethylene methyl methacrylate block copolymers, (e.g., NUKRELL polymers), polyurethanes (e.g., PELLATHANE polymers), silicone elastomers, polyester block copolymers such as HYTREL, rubber-based polyisobutylene, styrene, and styrene-butadiene and styrene-isoprene copolymers. Flexible polymers include polyethylene, polypropylene, and polyesters such as polyester terephthalate (PET), which may be provided as films or laminates. The thickness of the backing layer will normally be in the range of 0.01 to 0.15 mm, more normally 0.02 to 0.1 mm. The backing may optionally be pigmented (e.g., to resemble skin color).

Backing layer 12 has a cavity that serves as a reservoir or container for a liquid formulation of NTG, generally designated 14. Formulation 14 comprises NTG in a liquid vehicle. Examples of suitable liquid carriers are lower alkanols such as methanol, ethanol, isopropanol, glycols such as propylene glycol, and the like. Propylene glycol is preferred. The solubility parameter of propylene glycol is 12.6 $(cal/cm^3)^{\frac{1}{2}}$. The formulation may also contain additional ingredients such as a dye which may serve as an indicator of rupture of the reservoir. The NTG will normally comprise 2 to 20% by weight of the formulation, more normally 5 to 10% by weight. The total amount of NTG in the reservoir will normally be 50 to 300 mg, more normally 100 to 150 mg.

Directly underlying the cavity and backing layer is a pressure-rupturable layer 13. Layer 13 is sealed to the overlying backing layer 12 (and underlying layers to the microporous membrane layer 18) about the periphery of the cavity containing the NTG formulation 14. Layer 13 is also impermeable to the NTG formulation and serves as the basal wall of the reservoir. It is made of a material that may be ruptured with normal finger pressure such as aluminum foil coated with a heat sealable layer of ethylene vinyl acetate copolymer, polypropylene or polyethylene. Underlying layer 13 in registry with the reservoir is a hard, solid (incompressible) body 15 to which finger pressure may be applied to facilitate the rupture or tearing of layer 13 below the reservoir to release the liquid formulation of NTG from the reservoir. The body is smaller in dimension than the cavity containing the NTG solution. It will typically be made from hard materials such as polycarbonate, polypropylene, or high density polyethylene.

Immediately below the rupturable layer 13 is a wick layer 16 that is capable of dispersing or spreading the liquid formulation of NTG transversely (parallel) to the basal surface of the device. The wick layer does not absorb or retain any substantial amount of the NTG formulation and functions merely to spread the formulation across the device. It is not a barrier to diffusion of the NTG from the reservoir to the skin surface. The wick layer is preferably made from a nonwoven polymeric fabric such as spun-bonded polyester. It will normally have a basis weight of 0.2 to 1 oz./yard$^2$, preferably 0.4 to 0.6 oz./yard$^2$. The wick layer must be capable of adhering to the adjoining layers of the device under conditions of use (i.e., in the presence of adsorbed NTG formulation) and be sealable (e.g., by heat) to the overlying layers and to the underlying microporous membrane.

Underlying the wick layer 16 is a first layer of a polymer adhesive layer 17 that is permeable to the NTG formulation. The diffusion coefficient of NTG in this layer will normally be $1 \times 10^{-7}$ to $1 \times 10^{-8}$ cm/sec. Its thickness will normally be 0.02 to 0.3 mm, more usually 0.02 to 0.15 mm.

The next layer is a microporous membrane layer 18. The material from which the membrane itself is made is substantially impermeable to the NTG formulation and to the adhesive of layers 17 and underlying adhesive layer 20. Examples of microporous materials are microporous polypropylene (CELGARD, Hoechst-Celanese), microporous polyethylene (COTRAN, 3M), and microporous polytetrafluoroethylene (TEFLON, Gortex). The membrane will typically have a pore volume in the range of 10% to 60%. The pores are filled with a polymer 19 that is substantially immiscible with the adhesive of layers 17 and 20 and has a solubility parameter within about two units (units expressed in $(cal/cm^3)^{\frac{1}{2}}$). The immiscibility of the polymer with the adhesive deters the adhesive from migrating into the pores during storage. The similarity of the solubility parameter of the polymer to the vehicle permits the NTG formulation to permeate through the polymer. An example of a polymer that may be used to fill the membrane pores is polyethylene oxide (m.w. 100,000 to 600,000). The thickness of the microporous membrane layer will normally be 0.001 to 0.1 mm.

As indicated, a second adhesive layer 20 underlies the microporous membrane. The second adhesive layer may have the same or different composition as the first layer. The thickness of the second adhesive layer will normally be 0.02 to 0.3 mm, more usually 0.02 to 0.15 mm. Examples of adhesives from which the adhesive layers 17 and 20 may be made are polysiloxanes, polyacrylates, polyurethanes, and ethylene-vinyl acetate copolymers.

A standard release liner layer 22 underlies the second adhesive layer.

The delayed onset devices of the present invention are designed to be worn for a one-day period and then replaced. In the case of NTG, the devices will normally be placed on the skin shortly before the individual goes to sleep at night. Thus, the period during which the wearer receives insignificant NTG will coincide roughly with the wearer's sleeping hours; whereas the period during which delivery is effected will coincide roughly with the wearer's waking hours. This pattern of delivery provides NTG when most needed—upon awakening and through the day—and allows the level of NTG in the wearer's circulation to wash out or decline during sleep so that tolerance to NTG is lessened.

In use, the device is removed from its packaging and gripped such that a force may be applied from the basal surface against the solid body 15 to cause the solid body to penetrate and rupture layer 13. The release liner layer is then removed and the device is placed on the skin with the basal layer of the second adhesive layer 20 in drug-delivery contact with the skin surface. The rupturing of layer 13 permits the liquid NTG formulation 14 to be released onto the wick layer 16. The adsorbent properties of the wick layer cause the liquid to be dispersed across (parallel to the basal surface) the device. The liquid then diffuses through the first adhesive layer, the polymer-filled pores of the microporous membrane layer, and the second adhesive layer. The NTG is released from the basal surface of the second adhesive layer into the skin. The extent of the delayed onset will depend upon the diffusion coefficients of the polymers forming the first and second adhesive layers, the thicknesses of those two layers, the porosity characteristics of the microporous membrane, the thickness of the microporous membrane, and the solubility parameter of the polymer filling the membrane pores. With the ranges of these parameters given above a delay of at least eight hours is achieved before skin flux of NTG reaches about 2 $\mu g/cm^2/hr$. During the delay period the NTG skin flux ranges between 0 and about 2 $\mu g/cm^2/hr$. After the delay period the skin flux rises steadily over the remainder of the 24-hour wearing period to a skin flux level of about 5 to 20 $\mu g/cm^2/hr$. These levels of skin flux are as measured by the in vitro diffusion; all studies described in the Examples, infra. The drug delivery area of the device (i.e., the basal surface) is normally in the range of 10–50 cm$^2$, preferably 15–25 cm$^2$.

The devices of the invention may be made by conventional lamination techniques. By way of example, a cavity of desired size is formed in a backing layer. The cavity is filled with a 10% solution of NTG in propylene glycol. The rupturable foil layer is then placed over the cavity. Two sheets of release liner are then coated on one side with adhesive to the desired thickness. One of these sheets is laminated to the wick layer and the release liner is removed. A polymer-filled microporous membrane is then laminated to the exposed side of the adhesive layer and the other adhesive-release liner subassembly is laminated to the other side of the polymer-filled microporous membrane. The pores of the membrane may be filled with the polymer either by coating the polymer from solution onto the membrane surface and heating the coated membrane, dipping the membrane into molten polymer, or placing films of the polymer on both sides of the membrane and hot-rolling the subassembly. Finally the backing-NTG reservoir, rupturable layer subassembly is laminated to the wick layer onto which a 1 cm diameter, 2 mm thick disc of polycarbonate has been placed and the assembly is heat-sealed about the periphery of the cavity, thereby heat-sealing the backing through to the microporous membrane layers.

The following examples further describe the invention. These examples are not intended to limit the invention in any manner.

EXAMPLE 1

Water-based acrylic adhesive (Flexcryl 1625, 69% solids) was coated onto a 0.003" thick siliconized polyester release liner film at a thickness of 0.005". The adhesive coating was cured at 70° C. for 30 min in order to remove water; cured thickness was 0.002" (5 mg/cm$^2$). Two such films were prepared.

About 2 g of a polyethylene oxide (PEO) powder (POLYOX WSRN-10 from Union Carbide Corp.) was dispersed into about 31 g of water with constant stirring over a period of 10 min. About 1% by weight of a nonionic surfactant (Triton X-100) was then added. The resulting mixture was coated onto a microporous membrane (CELGARD 2400 from Hoechst-Celanese) at 0.015". The coated membrane was exposed to 67° C. for 60 hr, in which time the CELGARD turned transparent.

One of the two adhesive coated release liner films was laminated to a polyester nonwoven (Reemay 2250). The release liner was removed and the filled CELGARD was laminated to this exposed surface such that the coated side faced the nonwoven. The other side was laminated to the second adhesive film. A disc of this multilaminate was die-cut and laminated to the stratum corneum side of a disc of human cadaver epidermis, using the second adhesive.

A disc of the skin/multilaminate composite was mounted on a glass diffusion cell (effective flux area 0.71 cm$^2$) with the skin side facing the receptor compartment. The donor was 37 μl of a 10% nitroglycerin solution in propylene glycol (SDM 27 from ICI Americas). This solution was placed in the donor compartment directly in contact with the nonwoven. The donor compartment was then occluded, and the cell maintained at 32° C. Samples of the receiving solution were taken periodically and analyzed by HPLC to determine the amount of nitroglycerin permeated in unit time. The experiment was repeated exactly, substituting Nitro-Dur, a commercially available transdermal device, for the multilaminate layer and nitroglycerin vehicle.

Figure 2:
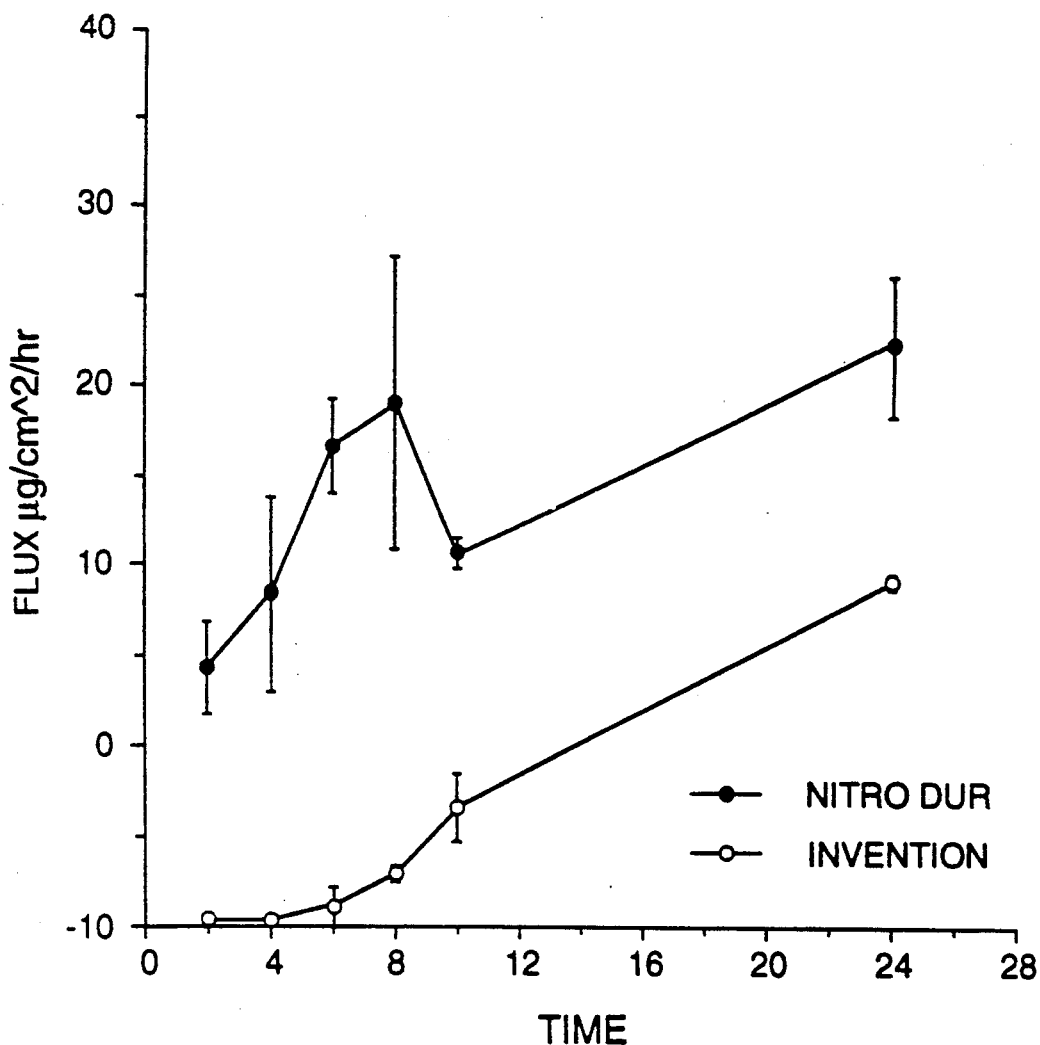
FIG. 2 is a graph of the results of the tests described in Example 1.

As shown in FIG. 2, Nitro-Dur reached substantial flux in 2-4 hr after administration, whereas the composite of the invention delayed full onset to 8 hr after administration.

EXAMPLE 2

Films of polyethylene oxide (PEO) were prepared by pouring a uniform layer of the powder onto the release side of a 0.003" thick siliconized polyester film. A second siliconized polyester film is then placed release side down on top of the PEO powder. This was pressed on a Carver press for 4 minutes at 100° C. and 24,000 psi between two stainless steel plates. Two PEO films of approximately 3 mils were prepared. The microporous membrane (CELGARD 2400 from Hoechst-Celanese) was sandwiched between these two PEO films and pressed on the Carver press for 4 minutes at 100° C. and 20,000 psi. This creates the pore-filled microporous membrane. An excess of PEO is used resulting in a layer of PEO on either side of the microporous membrane. Water-based acrylic adhesive (Flexcryl 1625, 69% solids) was coated onto a 0.003" thick siliconized polyester film at a thickness of 0.005". The adhesive coating was cured at 70° C. for 30 minutes in order to remove all of the water; cured thickness was 0.002" (5 mg/cm$^2$). Two adhesive films were prepared. The pore-filled microporous membrane is laminated to the one adhesive layer. The second adhesive film was laminated to the polyester nonwoven (Reemay 2250). The siliconized release liner is removed and the adhesive with the nonwoven is then laminated to the exposed microporous membrane surface. A disc of this multilaminate was die-cut and tested in skin flux studies as in Example 4, including comparison testing with Nitro-Dur.

The results were substantially the same as those for Example 1.

While the invention has been exemplified in terms of an embodiment for administering NTG, it may also be used to administer other drugs in a delayed onset regimen. Drugs which may be advantageously administered in such a regimen include other vasodilators, analgesics, contraceptives, appetite suppressants, growth factors, and the like. Other modifications of the above-described modes for carrying out the invention that are obvious to those of skill in the fields of transdermal drug delivery device design, materials science, polymer chemistry and related fields are intended to be within the scope of the following claims.

We claim:

1. A device for administering a drug transdermally following application of the device to a subject's skin wherein the delivery of drug is delayed at least about six hours after said application comprising in combination:
   (a) a nonrupturable backing layer forming the top surface of the device:
   (b) a pressure rupturable reservoir underlying (a) and containing the drug dissolved in a liquid vehicle;
   (c) an adsorbent wick layer underlying (b) for dispensing the drug once the reservoir is ruptured;
   (d) a layer of a drug permeable polymer adhesive underlying (c);
   (e) a microporous polymer membrane underlying (d), the polymer of which is impermeable to the solution of drug in the liquid vehicle;
   (f) a layer of a drug permeable adhesive polymer underlying (e) and forming the basal layer of the device wherein the pores of the membrane are filled with a polymer that is substantially immiscible in the polymers of (d) and (f), and has a solubility parameter that is within two units of the solubility parameter of the vehicle, wherein it initially takes at least about six hours for the drug to diffuse to the skin from the reservoir once the reservoir is ruptured and the device is applied to the skin.

2. The device of claim 1 wherein the reservoir is defined by a cavity formed between the backing layer and a pressure rupturable layer overlying the wick layer.

3. The device of claim 2 including means for transmitting manually applied pressure to the pressure rupturable layer.

4. The device of claim 3 wherein the means is an incompressible body underlying the pressure rupturable layer.

5. The device of claim 4 wherein the pressure rupturable layer is a metal foil layer.

6. A delayed onset device for administering nitroglycerin transdermally to a subject's skin comprising in combination:

(a) a nonrupturable backing layer forming the top surface of the device;

(b) a pressure rupturable reservoir underlying (a) and containing a solution of nitroglycerin in propylene glycol;

(c) an adsorbent wick layer underlying (b) for dispersing the nitroglycerin once the reservoir is ruptured;

(d) a first layer of a nitroglycerin permeable polymer adhesive underling (c);

(e) a microporous polymer membrane underling (d) the polymer of which is impermeable to the solution of nitroglycerin;

(f) a second layer of nitroglycerin permeable adhesive polymer underlying (e) and forming the basal surface of the device, wherein the pores of the membrane are filled with a polymer that is substantially immiscible in the adhesive polymers of (d) and (f) and has a solubility parameter within two units of the solubility parameter of propylene glycol and it initially takes at least about eight hours for the nitroglycerin to diffuse to the skin from the reservoir once the reservoir is ruptured and the device is applied to the skin.

7. The device of claim 6 wherein the polymer filling the pores of the membrane is high molecular weight polyethylene oxide.

8. The device of claim 7 wherein the diffusion coefficient of nitroglycerin in the adhesive polymers of (d) and (f) are $1 \times 10^{-7}$ cm/sec to $1 \times 10^{-8}$ cm/sec.

9. The device of claim 8 wherein the adhesive polymer is an acrylic polymer.

10. The device of claim 6 wherein the skin flux during said at least about six hours is less than 2 $\mu$g/cm$^2$/hr and thereafter rises to about 5 to 20 $\mu$g/cm$^2$/hr.

11. The device of claim 6 wherein the reservoir is defined by a cavity formed between the backing layer and a pressure rupturable layer overlying the wick layer.

12. The device of claim 11 including means for transmitting manually applied pressure to the pressure rupturable layer.

13. The device of claim 12 wherein the means is an incompressible body underlying the pressure rupturable layer.

14. The device of claim 9 wherein the skin flux during said at least about six hours is less than 2 $\mu$g/cm$^2$/hr and thereafter rises to about 5 to 20 $\mu$g/cm$^2$/hr.

15. The device of claim 1 wherein the drug is a vasodilator, analgesic, contraceptive, appetite depressant, or growth factor; the pressure rupturable reservoir is comprised of a metal foil coated with a layer of a heat-sealable polymer; the wick layer is nonwoven; and the material forming the microporous membrane is polypropylene, polyethylene, or polytetrafluoroethylene.

16. The device of claim 15 wherein the metal foil is aluminum foil and the heat-sealable polymer is ethylene vinylacetate copolymer, polyethylene, or polypropylene.

17. The device of claim 6 wherein the pressure rupturable reservoir is comprised of a metal foil coated with a layer of a heat-sealable polymer; the wick layer is nonwoven; the polymer filling the pores of the microporous membrane is polyethylene oxide; and the material forming the microporous membrane is polypropylene, polyethylene, or polytetrafluoroethylene.

18. The device of claim 17 wherein the metal foil is aluminum foil and the heat-sealable polymer is ethylene vinylacetate copolymer, polyethylene, or polypropylene.

* * * * *